United States Patent [19]
Wilbur et al.

[11] Patent Number: 5,402,264
[45] Date of Patent: Mar. 28, 1995

[54] CLEANING APPARATUS FOR LIGHT TUBE IN AN OPTICAL INSPECTION SYSTEM

[75] Inventors: John H. Wilbur; Calvin G. Gray, both of Medford, Oreg.

[73] Assignee: Simco/Ramic Corporation, Medford, Oreg.

[21] Appl. No.: 98,646

[22] Filed: Jul. 28, 1993

[51] Int. Cl.⁶ ........................ G02B 27/00; F21V 33/00
[52] U.S. Cl. ..................................... 359/508; 15/256.5
[58] Field of Search ............... 359/508, 507; 15/256.5, 15/256.51

[56] References Cited

U.S. PATENT DOCUMENTS

| | | | |
|---|---|---|---|
| 3,145,249 | 8/1964 | Meltzer | 359/508 |
| 3,495,366 | 2/1970 | Allen | 359/508 |
| 4,285,090 | 8/1981 | Jurkowski | 15/256.51 |
| 5,068,770 | 11/1991 | Baziuk | 362/61 |
| 5,161,055 | 11/1992 | Blechschmidt | 359/508 |

OTHER PUBLICATIONS

Key Technology, Inc., brochure entitled "ColorSort ® II: A Profile in Productivity" (1991).

*Primary Examiner*—Jon W. Henry
*Attorney, Agent, or Firm*—Stoel Rives Boley Jones & Grey

[57] ABSTRACT

An optical inspection system (10) has an inspection region (20) through which articles (12) pass and are illuminated by illumination (22) provided by an illumination source (30). The source is shielded from the inspection region by a protective shield or tube (32) transmissive of the illumination. A cleaning element (42), such as a plastic string, contacts a major surface (45) of the tube and dislodges contaminants (63) from the major surface as the tube rotates. The cleaning element has an active portion (60) held in contact with the major surface by tension in the cleaning element applied at tension locations (56, 58). The cleaning element describes part of a spiral or helix; it preferably occupies less than about 360 degrees, more preferably between about 30 and about 270 degrees, and still more preferably about 120 to about 240 degrees, of arc measured about the axis of the tube. The cleaning element flexes significantly under compression but remains taut under tension; it may be a monofilament or of woven construction; it has a maximum cross-sectional dimension $D_c$ that is much less than the maximum cross-sectional dimension $D_T$ of the tube.

21 Claims, 3 Drawing Sheets

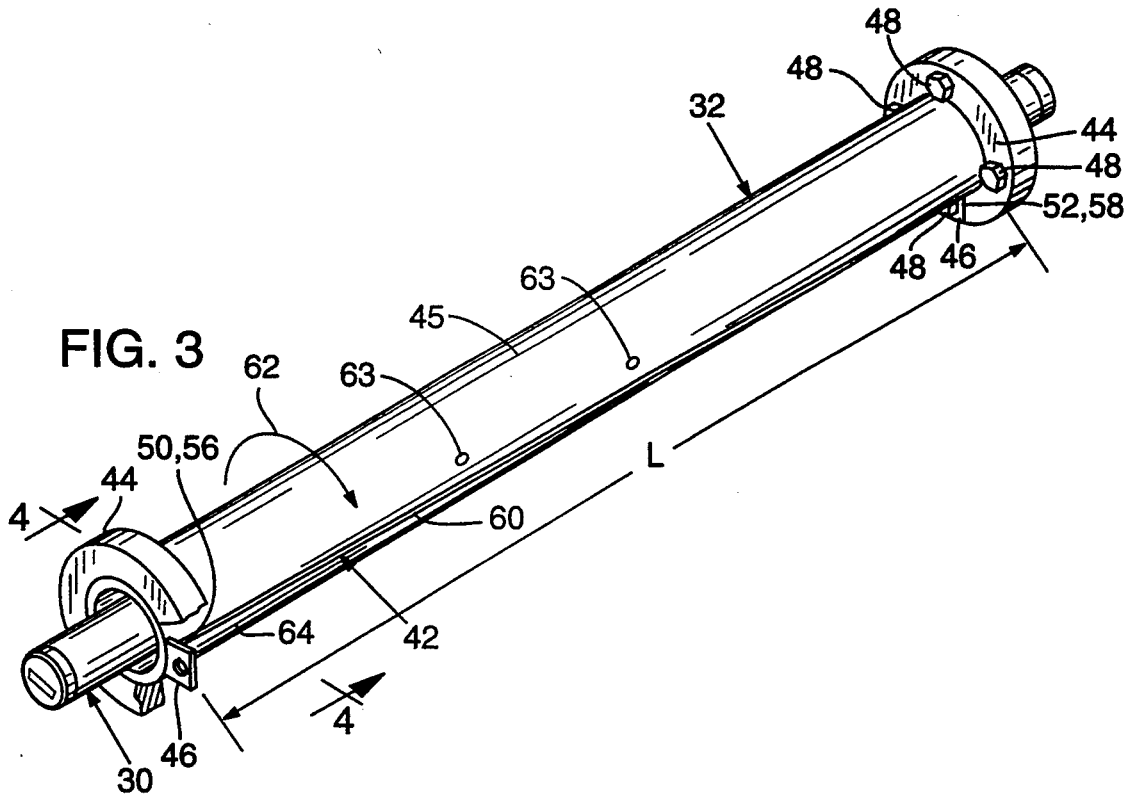
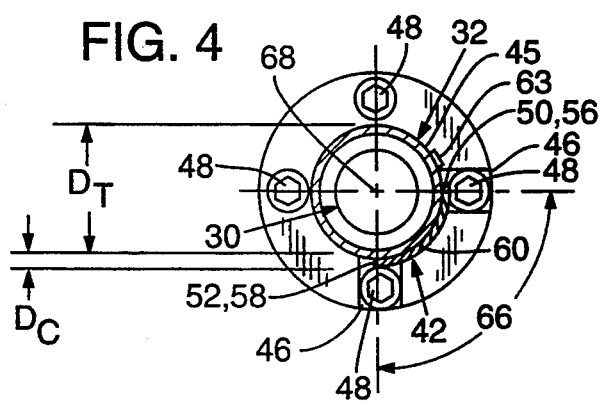

CLEANING APPARATUS FOR LIGHT TUBE IN AN OPTICAL INSPECTION SYSTEM

TECHNICAL FIELD

The present invention pertains to illumination systems for optical inspection systems such as automated bulk processing systems.

BACKGROUND OF THE INVENTION

Optical inspection systems such as automated bulk processing systems are used for determining optical characteristics of articles. In such a system a conveyor moves the articles through an inspection region, where they are illuminated with light produced by an illumination source. An inspection station including cameras or other optical detection devices views the illuminated articles and determines characteristics of the articles based on that view. The inspection system ordinarily also performs operations on the articles according to instructions from a logic unit; the instructions are based on the determined characteristic of the articles. The inspection station sends signals to a sorting or treatment station where the articles are sorted or treated by category. For example, defective or foreign articles may be removed from the flow of articles carried by the conveyor. The most con, non method of removal is by directing an accurately timed blast of a fluid, such as water or compressed air, at an article to be sorted so as to direct it out of the flow of acceptable articles.

Automated bulk processing systems can perform a variety of tasks such as inspecting or sorting bulk articles including raw or processed fruit, vegetables, wood chips, recycled plastics, and other similar products. The articles may be inspected for optically-detectable characteristics such as size, color, or shape. The systems can rapidly separate very large quantities of articles into two or more categories.

The effectiveness of such bulk processing equipment is greatly affected by the level and consistency of the illumination provided to the articles as they move through the inspection region. One of the factors determining the level and consistency of the illumination is whether the sources of the illumination have clean surfaces. Illumination sources used in optical inspection systems are typically fluorescent light tubes separated from the inspection region by a protective tube transmissive of the illumination. The protective tube is most commonly of the polycarbonate plastic sold by General Electric under the trademark LEXAN ® or by Rohm & Haas.

Keeping the protective tube clean is especially important when the inspection region is not located on a conveyor belt but rather is a region of space through which articles pass by inertia after leaving a rapidly moving conveyor belt. In such a system contaminants such as dust become airborne and are especially likely to settle on exposed surfaces of the protective tubes. Moreover, when the articles are treated in a region of space through which they move, the processes of treatment (such as directing a blast of water or compressed air at an unwanted wood chip) can generate further contaminants and air currents, which increases the possibility that contaminants will settle on exposed surfaces of protective shields. To keep the protective tube clean, it is commonly rotated during operation of the inspection system, and a wiper is held against a surface of the protective tube during the rotation.

A wiper presently in use resembles a squeegee and is a plastic blade attached to a metal bar by spaced apart bolts. This type of wiper is effective in cleaning the tube where the plastic blade has good contact with the surface of the protective tube, particularly in applications where the contaminants or the surface of the protective tube are wet. However, such contact depends on the straightness of the metal bar that holds the plastic blade and on the extent to which, during use, the plastic of the blade expands and thus pulls away from the protective tube between the bolts with which the plastic blade is attached to the metal bar or loses uniform contact with the tube by wearing. Where the plastic blade contacts the surface of the protective tube, it causes scratching of that surface, in part by forcing contaminants into the surface; where it does not contact the surface of the protective tube, it is less effective in dislodging contaminants from that surface. When its contact with the surface of the tube is variable, it causes a variable degree of scratching. These problems lead to an uneven pattern of removal of contaminants from, and an uneven degree of scratching of, the surface of the protective tube. Both of those factors cause an uneven level of light transmission along the length of the tube, which interferes with proper illumination of articles being inspected.

There is thus a need to provide for optical inspection systems such as bulk optical processing systems a protective shield from which contaminants are removed throughout the illumination portion (the portion through which light reaches the part of the inspection region at which articles are optically inspected) of the protective shield in a reliable and consistent manner and without scratching the protective shield.

SUMMARY OF THE INVENTION

An object of the present invention is, therefore, to provide for an optical inspection system an apparatus for cleaning the exposed surface of a protective tube that does not cause uneven scratching of, or uneven contaminant removal from, the surface.

Another object of this invention is to provide for an optical inspection system an apparatus for cleaning the exposed surface of protective tubes that causes less scratching of the surface of the tubes than squeegee-type wipers.

The invention meets the need, and satisfies the technical objectives, set forth above by providing a new and improved apparatus for cleaning the exposed or major surfaces of protective tubes in an inspection system. The inspection system has an inspection region in which articles in motion through the region are illuminated by illumination produced by an illumination source such as a fluorescent lamp tube. A protective shield is disposed between the lamp and the region; it is transmissive of the illumination and has a major surface including an illumination portion, through which illumination propagates from the lamp to the part of the inspection region at which articles are optically inspected.

A cleaning element, such as a thin plastic string, has first and second tension locations and an active portion between the tension locations; the active location is held in contact with the major surface by tension in the cleaning element. A movement system is operable to produce relative movement of the major surface and the active portion. The tension causes the active portion to exert sufficient pressure on the major surface to dislodge contaminants from the surface as a result of the movement. This produces a swept portion of the surface from which contaminants have been dislodged. The swept portion becomes the illumination portion of the major surface. The swept portion preferably rotates with the major surface into the illumination portion.

The pressure of the active portion on the major surface is preferably insufficient to cause significant scratching of the major surface. The active portion is preferably in contact with the major surface over a substantial portion of a major dimension of the major surface.

When the protective shield is (as is most common) a tube having an axis and an exterior surface defining the major surface, the cleaning element preferably defines a portion of a spiral or helix with respect to the major surface. The cleaning element preferably occupies less than about 360 degrees, more preferably between about 30 and about 270 degrees, and still more preferably between about 120 and about 240 degrees, of arc measured about the axis; its area of contact with the major surface thus forms a portion of a spiral or helix with a pitch or repetition length that is preferably equal to or longer than the length of the tube.

The cleaning element meets the need and satisfies the objects set forth above primarily because its active portion is held in contact with the major surface by tension in the active portion rather than by compressive forces such as are found in squeegee-type wipers. The cleaning element is also preferably flexible so that it can twist or stretch slightly; as a result, the force it exerts on the major surface remains substantially uniform even when the cleaning element encounters contaminants on the major surface. This allows the active portion to dislodge contaminants with substantially equal efficiency throughout the active portion. The cleaning element also causes contaminants to fall off the major surface rather than to bore into the major surface as is the case with squeegee,type wipers.

Additional objects and advantages of the present invention will be apparent from the detailed description of preferred embodiments thereof, which proceeds with reference to the accompanying drawings.

BRIEF DESCRIPTION OF THE DRAWINGS

FIG. 3 is a partly-cut-away perspective view of a lamp and its rotatable protective tube showing a cleaning element according to the invention.

FIG. 4 is a cross-sectional view taken along lines 4—4 of FIG. 3, illustrating the extent of arcuate coverage of the protective tube by the cleaning element.

DETAILED DESCRIPTION OF PREFERRED EMBODIMENTS

Figure 1:
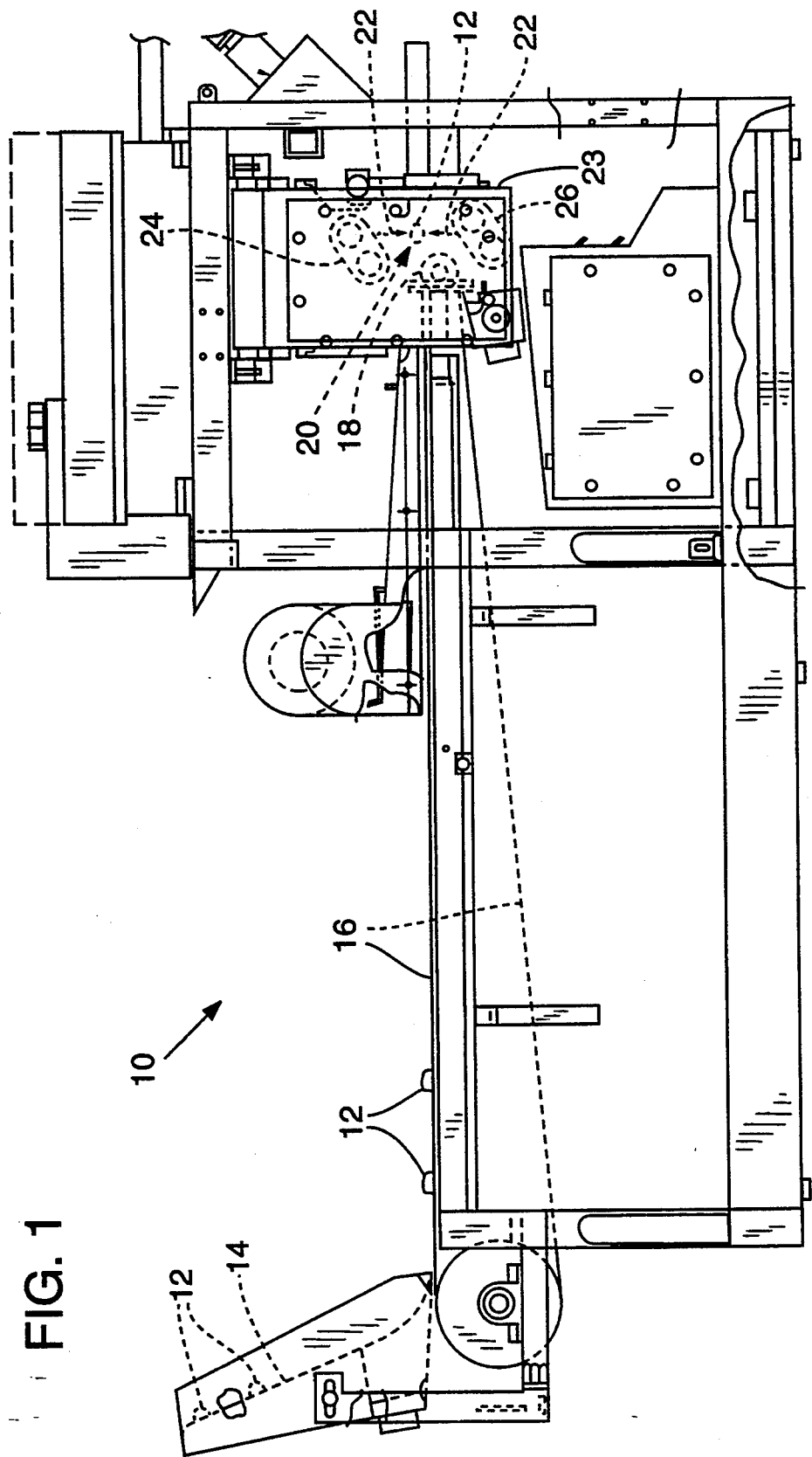
FIG. 1 is a side elevation view of an automated bulk processing system designed for sorting wood chips.

FIG. 1 is a side elevation view of an optical inspection system or automated bulk processing system or pulpwood sorter 10 designed for sorting wood chips. Articles or pulpwood chips 12 feed from an infeed shaker (not shown) into an acceleration chute 14, which deposits them on a conveyor belt 16 that typically moves at a speed of approximately 150–365 meters (500–1200 feet) per minute. Chips 12 progress on conveyor belt 16 until it turns at pulley 18; at that point chips 12 move by inertia through the air through an inspection region 20.

Illumination 22 for chips 12 in inspection region 20 is provided by a light module 23 having respective upper and lower illumination units 24 and 26. FIG. 1 shows illumination units 24 and 26 with illumination sources in offset position with respect to the path of articles 12. An inspection station or stations (not shown) view chips 12 under illumination 22 in inspection region 20 and determine characteristics of individual chips 12 based on automated analysis of that view. The inspection station or stations then issue commands to a treatment station (not shown), which sorts chips 12 by applying a blast of a fluid such as water or compressed air to those individual chips 12 which are to be sorted out of the flow of acceptable chips.

Figure 2:
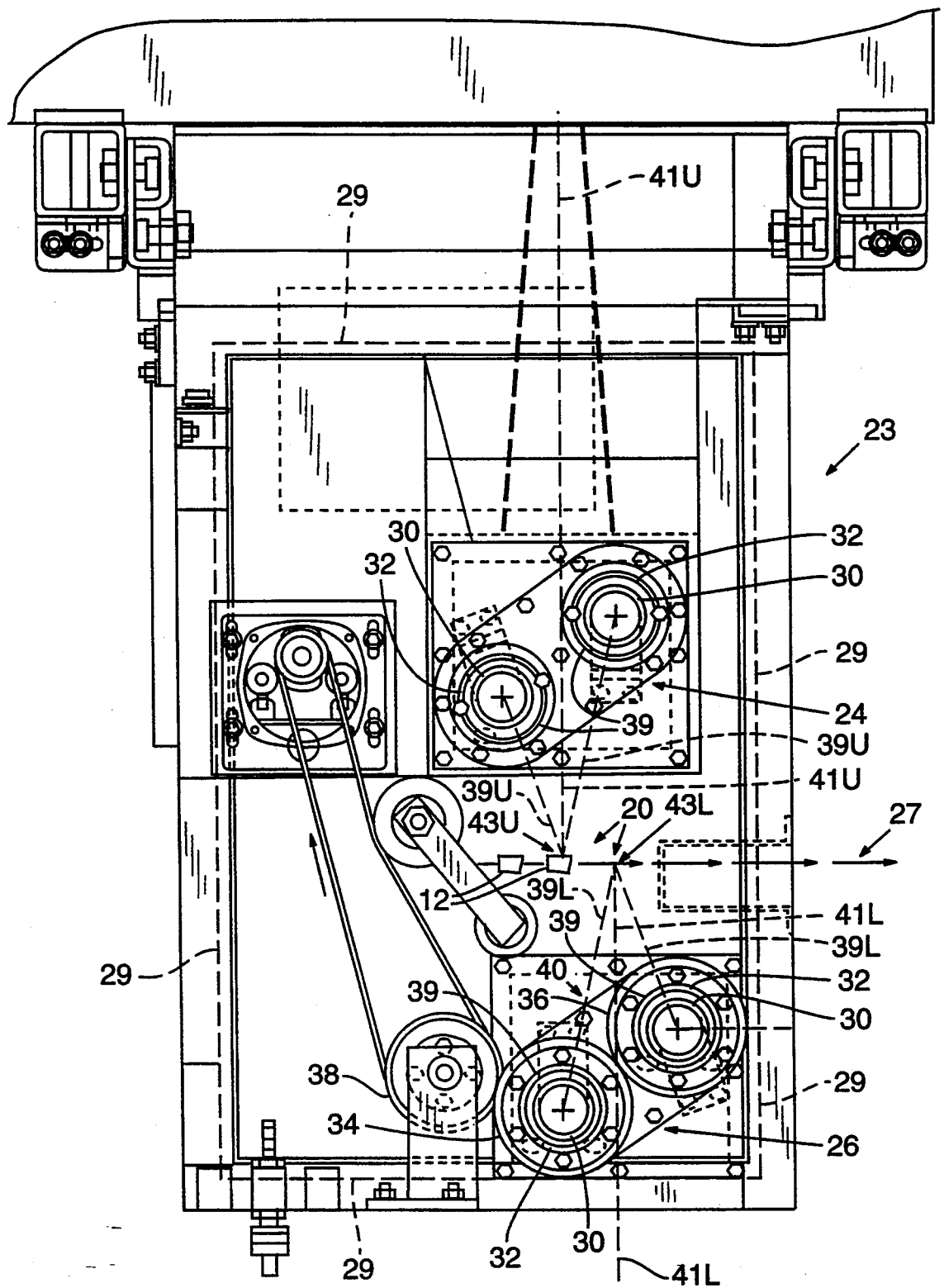
FIG. 2 is an enlarged side elevation view of part of the processing system of FIG. 1, showing the inspection region with fluorescent lamps and their rotatable protective tubes.

FIG. 2 is an enlarged side elevation view of light module 23 (with an inspection cover removed from the area shown by dashed lines 29) of sorter 10 of FIG. 1, showing inspection region 20 with upper and lower illumination units 24 and 26. FIG. 2 also shows illumination units 24 and 26 in offset position with respect to the approximate path or trajectory 27 of articles 12. Illumination units 24 and 26 may optionally be configured in parallel position (not shown); parallel position differs from offset position in that each of the two lamps 30 and tubes 32 in illumination unit 24 and also in illumination unit 26 is level with the other. In parallel position lamps 30 and tubes 32 are aligned with their lengthwise extension perpendicular to path 27, as shown in FIGS. 1–2 for offset position. The choice between offset (FIGS. 1-2) and parallel positions depends on the characteristics of articles 12.

Each illumination unit 24 and 26 includes two illumination sources or fluorescent lamps 30, each of which is surrounded by a protective shield or tube 32 that is transmissive of illumination 22 (FIG. 1) produced by lamp 30. Tubes 32 are preferably of polycarbonate plastic such as LEXAN ® because of its surface hardness and toughness but in some applications may be of a softer plastic, such as acrylic, that is transmissive of illumination 22, if the softer plastic resists scratching sufficiently for the applications. Tubes 32 of lower illumination unit 26 are attached to drive disks 34 and 36, respectively, which have mating gear teeth. Drive disk 34 has gear teeth that mate with gear teeth on a drive wheel 38, which rotates so as to cause drive disks 34 and 36 (and accordingly also the attached tubes 32) to rotate up from the region 40 between them. Such a direction of rotation helps to reduce the possibility of chips 12 becoming lodged between tubes 32 of lower illumination unit 26 and consequently either impeding rotation of those tubes 32 or even scratching or breaking the surface of those tubes 32.

Tubes 32 of upper illumination unit 24 are not shown as mounted on drive disks or as otherwise equipped for rotation. Their location above inspection region 20 reduces the possibility that contaminants may settle on their surfaces and thus reduces the need for apparatus for keeping their surfaces clean of contaminants. However, tubes 32 of upper illumination unit 24 can be equipped with rotation and cleaning apparatus according to the invention if desired.

An upper line scan camera (not shown) scans in a plane 41U that passes between the two upper tubes 32 and intersects path 27 at scan location 43U. A lower line scan camera (also not shown) scans in a plane 41L that passes between the two lower tubes 32 and intersects path 27 at scan location 43L. Lines 39U show the path from the center of tubes 32 of upper illumination unit 24 to scan location 43U; lines 39L show the path from the center of tubes 32 of lower illumination unit 26 to scan location 43L. Tubes 32 of upper and lower illumination units 24 and 26 each have an illumination portion 39 lying about 90 degrees to either side of the intersection of their respective lines 39U and 39L with the exterior surface of tubes 32.

FIG. 3 is a partly-cut-away perspective view of a lamp 30 and tube 32 of lower illumination unit 26 showing a cleaning element 42, such as a plastic string, according to the invention. Each end of tube 32 is rotatably received within a collar 44 attached to an object (not shown) such as a side of light module 23 (FIGS. 1–2) that does not rotate with tube 32; one or both ends of tube 32 are also mounted in any convenient way (not shown) to a drive disk 34 or 36 (FIG. 2). Each collar 44 has a seal (not shown) of a flexible material such as rubber that keeps dust or other contaminants from entering tube 32. As drive disk 34 or 36 rotates, tube 32 rotates freely within collar 44. Tube 32 has an exterior surface 45 and a major dimension or length n between collars 44. Skilled persons will appreciate that, although tube 32 is shown as separate from lamp 30, tube 32 could be the hard exterior surface of lamp 30.

A cleaning element mounting device or bracket 46 is affixed to each collar 44 in any convenient way such as with a mounting bolt 48. Bracket 46 is mounted close to surface 45 so that cleaning element 42 contacts surface 45 over most of length L but not so close as to create a risk that bracket 46 would scratch surface 45. Cleaning element 42 has first and second ends 50 and 52 attached to mounting brackets 46. Ends 50 and 52 also constitute respective first and second tension locations 56 and 58. Cleaning element 42 is mounted to brackets 46 under tension; as a result, brackets 46 exert on ends 50 and 52 respective resultant forces that are directed substantially collinearly with and outward from cleaning element 42 at respective ends 50 and 52. Ends 50 and 52 and tension locations 56 and 58 also apply forces to the part of cleaning element 42 lying between them. Those forces place that part of cleaning element 42 under tension. An active portion 60 of cleaning element 42 contacts surface 45 of tube 32 as a result of that tension and is held in contact with major surface or tube exterior surface 45 by that tension. The tension should be high enough to keep cleaning element 42 in close contact with surface 45 but not so high as unduly to shorten the service life of cleaning element 42. Preferably the tension is as low as it can be consistent with maintaining good contact between cleaning element 42 and surface 45 across most of surface 45.

As tube 32 rotates (FIG. 2 and its description) in direction 62, active portion 60 dislodges contaminants 63 from surface 45. Swept surface 64 is the portion of surface 45 from which cleaning element 42 has dislodged contaminants 63. As tube 32 rotates, the part of surface 45 that is in illumination portion 39 (FIG. 2) moves with any contaminants adhering to it out of illumination portion 39, and swept surface 64 rotates around lamp 30 and into illumination portion 39. This ensures continuous movement of uncleaned portions of surface 45 out of illumination portion 39 and of the swept portion into illumination portion 39. The rotation rate of tube 32 is selected so that it is unlikely that contaminants adhered to surface 45 will remain in illumination portion 39 for a time long enough to have an adverse effect on the operation of the inspection system.

FIG. 4 is a cross-sectional view taken along lines 4—4 of FIG. 3. As shown in FIG. 4, tube 32 has a maximum cross-sectional dimension or diameter $D_T$, and cleaning element 42 has maximum cross-sectional dimension or diameter $D_c$, in each case measured perpendicular to the respective length. Cleaning element 42 extends through an arc or twist angle 66 measured about axis 68 of tube 32 and thus defines a portion of a spiral or helix. Arc or twist angle 66 may exceed 360 degrees, but it is preferably less than about 360 degrees, more preferably between about 30 degrees and 270 degrees, and still more preferably between about 120 and about 240 degrees. A larger arc or twist angle 66 provides more even tension in cleaning element 42 and more uniform pressure of active portion 60 or surface 45; it also allows cleaning element 42 to come in contact with exterior surface 45 closer to brackets 46. However, arc or twist angle 66 should not be so great that cleaning element 42 tightens on surface 45 and either significantly retards rotation of tube 45 or breaks. Cleaning element 42 is preferably mounted with its highest end at or below the horizontal center line of tube 32 so that gravity assists contaminants dislodged by cleaning element 42 to fall off tube 32.

Cleaning element 42 thus extends between ends 50 and 52 to define a portion of a spiral or helix having a relatively long pitch or repetition interval. As indicated by the preferable ranges of arc 66, the pitch or repetition interval of the spiral or helix is preferably equal to or greater than about the length L of tube 32.

Active portion 60 should constitute all or nearly all of cleaning element 42 so that surface 45 is swept over all or nearly all of its length L (FIG. 3) to assure that the illumination provided by tube 30 remains substantially unaffected by the presence of contaminants on unswept portions of surface 45. Tube 32 is preferably a tube of circular cross-section and constant diameter (as shown). Surface 45 is preferably convex with respect to lamp 30.

Cleaning element 42 is preferably of a character that flexes significantly under compression but remains taut under tension. It also is preferably flexible so that it can twist or stretch slightly; as a result, the force it exerts on major surface 45 remains substantially uniform even when it encounters contaminants 63. This allows active portion 60 dislodge contaminants 63 with substantially equal efficiency throughout its length. It also is preferably of a character that is softer than surface 45 so that cleaning element 42 is unlikely to scratch surface 45 and so that any wear occurs on cleaning element 42, which is inexpensive and easily replaced, rather than on tube 32. $D_c$ is preferably much less than $D_T$. Cleaning element 42 may have a substantially circular cross-section. It may be a monofilament of a plastic or a woven string of a natural textile or synthetic fiber.

Cleaning element 42 is preferably mounted in a location other than in illumination portion 39 and especially should be mounted in a location that does not overlap illumination portion 39 for the part of illumination region 20 scanned by the cameras. Such a mounting keeps cleaning element 42 from affecting the intensity of illumination in inspection region 20. If cleaning element 42 is mounted on a tube 32 above inspection region 20 (such as in upper illumination unit 24 (FIGS. 1–2)), cleaning element 42 is preferably mounted above the center line of that tube to ensure that cleaning element 42 does not affect illumination for inspection region 20.

However, if the inspection system can be adjusted so as not to view as a defect or as a characteristic to be sorted or recognized any change in illumination level of articles 12 in inspection region 20 caused by the presence of cleaning element 42 in illumination portion 39, then cleaning element 42 may be present in illumination portion 39.

Cleaning element 42 is also preferably mounted in a fixed location with respect to illumination region 39. As an alternative, cleaning element 42 could itself be swept across a portion of the surface 45 of a tube that is either in rotation, or is stationary, with respect to inspection region 20.

Cleaning element 42 is also preferably mounted so that dislodged contaminants 63 fall away from inspection region 20. However, in some applications system 10 can sort accurately even if dislodged debris falls into inspection region 20.

Skilled persons will appreciate that the choice of material, shape, maximum cross-sectional dimension DC, hardness, tension, and arc 66 for cleaning element 42 depends on the type of contaminant 63 to be dislodged and on whether surface 45 of tube 32 is wet or dry when system 10 is in operation. For example, cleaning element 42 should not be of a dimension or material that allows contaminants 63 to hop or bridge over cleaning element 42 and reattach themselves to swept surface 64. Cleaning element 42 should cause contaminants to agglomerate near it and reach a sufficient weight to fall off by gravity. Cleaning element 42 may be formed of a substance that conducts electricity and be grounded.

In one implementation of the invention, tube 32 was of transparent polycarbonate plastic, had an outside diameter $D_T$ of approximately 6.35 centimeters (2.5 inches), a wall thickness of approximately 3.2 millimeters (⅛ inch), and a length of approximately 1.7 meters (66 ⅜ inches); cleaning element 42 was a single filament of plastic sold by the Arnold Company of Shelby, Ohio, as lawn or weed trimmer replacement string and had a substantially circular cross-sectional diameter $D_c$ of approximately 1.7 millimeters (0.065 inch); the rotation rate of tube 32 was approximately eight revolutions per minute; arc 66 occupied by cleaning element 42 was approximately 240 degrees (initially arc 66 was approximately 1080 degrees, corresponding to three turns of cleaning element 42 about tube 32, but at that value for arc 66 cleaning element 32 tightened against tube 32 and broke); tube 32 and cleaning element 42 were mounted below inspection region 20; and inspection system 10 was used for automated sorting of pulpwood chips derived primarily from at least partly debarked logs of several conifer species.

In another implementation of the invention, tube 32 was of transparent polycarbonate plastic, had an outside diameter $D_T$ of approximately 6.35 centimeters (2.5 inches), a wall thickness of approximately 3.2 millimeters (⅛ inch), and a length of approximately 1.7 meters (66-⅜ inches); the rotation rate of tube 32 was approximately eight revolutions per minute; arc 66 occupied by cleaning element 42 was approximately 90 degrees; tube 32 and cleaning element 42 were mounted below inspection region 20; and inspection system 10 was used for automated sorting of dry tobacco. Initially cleaning element 42 was a plastic monofilament sold as fishing line and had a substantially circular cross-sectional diameter $D_c$ of approximately 0.25 millimeters (0.010 inch); but this was not effective in removing tobacco dust from surface 45. The lawn or weed trimmer replacement line mentioned above was then substituted as cleaning element 42; the system then worked satisfactorily in removing the tobacco dust from surface 45 whether that surface was dry or wetted. However, rotation of tube 32 had to be stopped in that inspection system because, when tube 32 was rotated, nonuniformity in the construction of that tube 32 created lighting variations that interfered with proper sorting of the tobacco.

It will be apparent to skilled persons that many changes may be made to details of the specific embodiments of the invention described herein without departing from the underlying principles thereof. The scope of the invention should, therefore, be determined only by the following claims.

We claim:

1. An inspection system operable to determine characteristics of articles in motion through an inspection region according to automated analysis of a light pattern produced by illumination of the articles in the region by an illumination source, comprising:

a protective shield disposed between the source and the region, transmissive of the illumination, and having a major surface including an illumination portion;

a cleaning element having first and second tension locations and an active portion between the locations, the locations applying forces that create tension in the active portion, the active portion held in contact with the major surface by the tension; and a movement system operable to produce relative movement of the major surface and the active portions the tension sufficient to cause the active portion to exert sufficient pressure on the shield to dislodge contaminants from the major surface as a result of the relative movement and thereby to produce a swept portion of the major surface, the movement system further operable to cause the swept portion to be the illumination portion.

2. The system of claim 1, wherein the movement system is operable to move the shield so that the swept portion becomes the illumination portion.

3. The system of claim 2, wherein the active portion does not contact the illumination portion.

4. The system of claim 1, wherein the movement system is operable to move the active portion across the illumination portion to dislodge contaminants from the illumination portion.

5. The system of claim 1, wherein the relative movement is continuous during operation of the system.

6. The system of claim 1, wherein the pressure of the active portion on the major surface is insufficient to cause significant scratching of the major surface.

7. The system of claim 1, wherein the forces are as low as possible consistent with maintaining good contact between the active portion and the major surface during the relative movement.

8. The system of claim 1, wherein the major surface has a major dimension, and the tension locations are secured to respective first and second mounting locations so as to place the active portion in contact with the major surface over a substantial portion of the major dimension.

9. The system of claim 1, wherein the cleaning element is of a character that flexes significantly under compression but remains taut under tension.

10. The system of claim 1, wherein the major surface has a first hardness and the cleaning element has a second hardness less than the first hardness.

11. The system of claim 1, wherein the illumination source comprises a lamp tube, and the protective shield comprises a tube separate from the lamp tube.

12. The system of claim 1, wherein:
the protective shield comprises a tube having an exterior surface defining the major surface, and
the active portion defines a portion of a helix with respect to the exterior surface.

13. The system of claim 12, wherein the exterior surface is convex with respect to the source.

14. The system of claim 12, wherein the tube has a circular cross-section.

15. The system of claim 12, wherein the tube has an axis, and the cleaning element occupies less than about 360 degrees of arc measured about the axis.

16. The system of claim 12, wherein the tube has an axis, and the cleaning element occupies between about 30 degrees and about 270 degrees of arc measured about the axis.

17. The system of claim 12, wherein the tube hasan axis, and the cleaning element occupies between about 120 degrees and about 240 degrees of arc measured about the axis.

18. The system of claim 12, wherein the tube has a diameter, and the cleaning element comprises a line having a maximum cross-sectional dimension much smaller than the diameter.

19. The system of claim 18, wherein the line has a substantially circular cross-section.

20. An inspection system operable to determine characteristics of articles in motion through an inspection region according to automated analysis of a light pattern produced by illumination of the articles in the region by an illumination source, comprising:
a protective shield disposed between the source and the region, transmissive of the illumination, having a length, having first and second shield ends, and having a major surface including an illumination portion that occupies a substantial portion of the length;
a first mounting device located adjacent the first shield end and near the major surface;
a second mounting device located adjacent the second shield end and near the major surface;
a cleaning element having first and second cleaning element ends each attached to a respective one of the first and second mounting devices, and an active portion between the cleaning element ends, the devices applying to the cleaning element ends respective resultant forces that are directed substantially collinearly with and outward from the cleaning element at the respective cleaning ends; and
a movement system operable to produce relative movement of the major surface and the active portion, the forces sufficient to cause the active portion to contact the major surface and to exert sufficient pressure on the major surface to dislodge contaminants from the major surface as a result of the relative movement and thereby to produce a swept portion of the major surface, the movement system further operable to cause the swept portion to be the illumination portion.

21. An inspection system operable to determine characteristics of articles in motion through an inspection region according to automated analysis of a light pattern produced by illumination of the articles in the region by an illumination source, comprising:
a protective shield disposed between the source and the region, transmissive of the illumination, having a length, having first and second shield ends, and having a major surface including an illumination portion that occupies a substantial portion of the length;
a first mounting dayice located adjacent the first shield end and near the major surface;
a second mounting device located adjacent the second shield end and near the major surface;
a string having first and second string ends, each attached to a respective one of the first and second mounting devices, and an active portion between string ends, the devices applying forces to the string ends so as to cause the active portion to extend along the major surface and to define a portion of a helix having a pitch greater than about the length; and
a movement system operable to produce relative movement of the major surface and the active portion, the forces sufficient to cause the active portion to contact the major surface and to exert sufficient pressure on the major surface to dislodge contaminants from the major surface as a result of the relative movement and thereby to produce a swept portion of the major surface, the movement system further operable to cause the swept portion to be the illumination portion.

* * * * *